Figure 1:
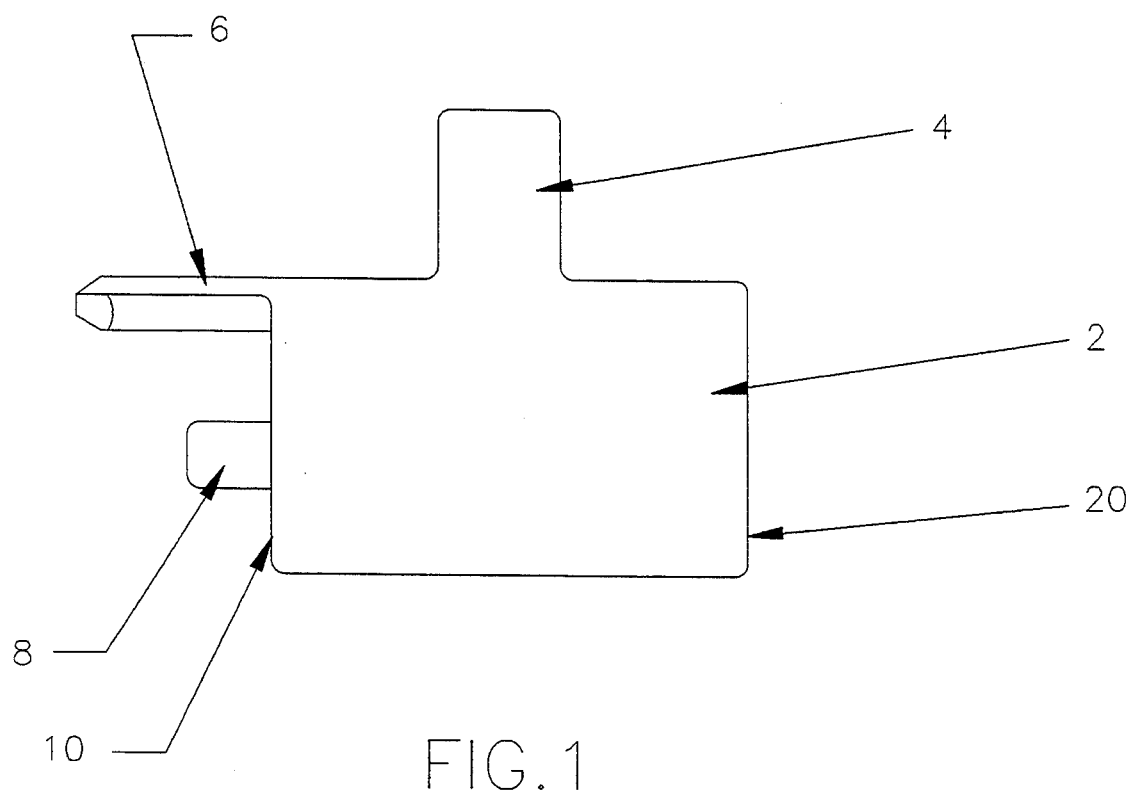
Figure 2:
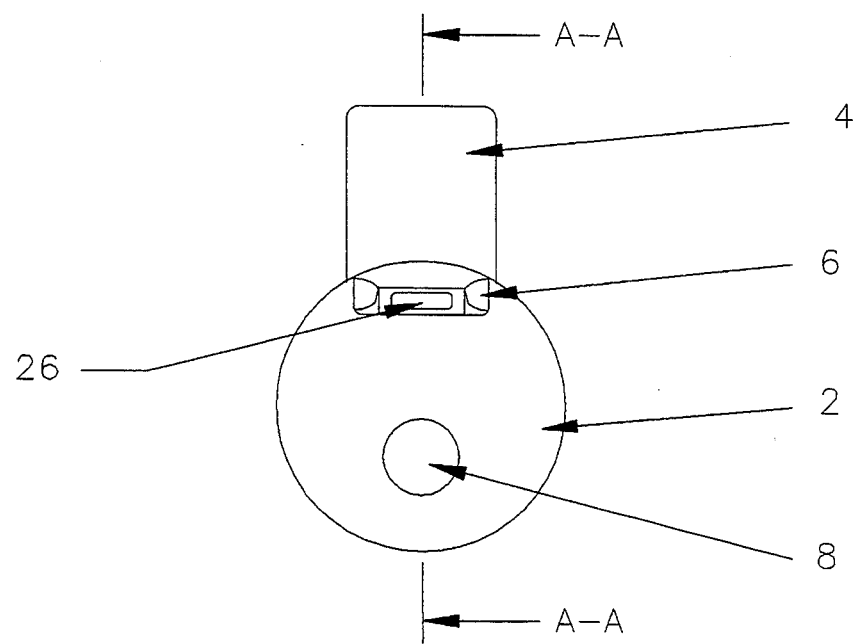

United States Patent [19]

Zechner

[11] Patent Number: 5,341,801
[45] Date of Patent: Aug. 30, 1994

[54] INHALER

[75] Inventor: Kurt Zechner, Allschwil, Switzerland

[73] Assignee: Sandoz Ltd., Basel, Switzerland

[21] Appl. No.: 983,012

[22] Filed: Nov. 30, 1992

[30] Foreign Application Priority Data

Dec. 3, 1991 [DE] Fed. Rep. of Germany ....... 4139806

[51] Int. Cl.⁵ ............................................. A61M 15/00
[52] U.S. Cl. .............................. 128/203.15; 128/203.23; 222/631
[58] Field of Search .................. 128/203.15, 203.23, 128/203.24, 203.12; 222/630, 634, 636, 361, 631; 406/73, 74, 67, 63; 141/67, 249, 260; 414/219, 220, 304, 323

[56] References Cited

U.S. PATENT DOCUMENTS

| 2,603,215 | 7/1952 | Arnow | 128/203.15 |
| 3,656,518 | 4/1972 | Aronson | 141/1 |
| 4,005,668 | 2/1977 | Washington | 141/67 |
| 5,113,855 | 5/1992 | Newhouse | 128/203.12 |

FOREIGN PATENT DOCUMENTS

| 484267 | 6/1952 | Canada | 222/360 |
| 2926659 | 1/1981 | Fed. Rep. of Germany | 128/203.15 |
| 1503827 | 8/1989 | U.S.S.R. | 128/203.15 |
| 9007351 | 7/1990 | World Int. Prop. O. | 128/203.15 |
| 9106333 | 5/1991 | World Int. Prop. O. | 128/203.15 |
| 9112895 | 9/1991 | World Int. Prop. O. | 128/203.15 |

Primary Examiner—Edgar S. Burr
Assistant Examiner—Eric P. Raciti
Attorney, Agent, or Firm—Robert S. Honor; Melvyn M. Kassenoff; Carl W. Battle

[57] ABSTRACT

An inhaler for delivering metered doses of a particulate drug. The inhaler is formed of a housing, a drug reservoir attached to the housing to contain multiple doses of the particulate drug, a drug transporting slide in the housing that contains a metering chamber of volume corresponding to a desired dose of the drug, and a vacuum pump that creates a partial vacuum in the metering chamber. The drug transporting slide is movable from a load position, in which it communicates with the drug reservoir to receive in its metering chamber drug from the drug reservoir, to a release position in which it communicates with an air outlet passage to release drug from the metering chamber into the air outlet passage. The drug reservoir has an air permeable portion that permits air flow into the drug reservoir but prevents drug escape. In use, the vacuum pump draws a dose of drug into the metering chamber. The drug transporting slide then moves to deposit the drug in the outlet passage for inhalation.

12 Claims, 4 Drawing Sheets

INHALER

This invention relates to an inhaler that is able to dispense metered doses of a particulate drug.

Many types of inhalers that dispense particulate medicaments are known but all have difficulty in reproducibly dispensing metered dosages of powdered medicaments; particularly those that are prone to agglomerate. Some of these difficulties can be overcome by formulating the drugs with appropriate excipients, or in suitable capsules, but this is not always possible or desirable.

It is therefore an object of this invention to provide an inhaler that is simple in construction and is able to reproducibly dispense metered doses of appropriately formulated drugs.

Accordingly, in one aspect this invention provides an inhaler suitable for delivering metered doses of a particulate drug. The inhaler comprises:

a housing having an air inlet and an air outlet passage communicating with the air inlet;

a drug reservoir attached to the housing to contain multiple doses of the particulate drug, the drug reservoir having an air permeable portion that permits air flow into the drug reservoir but prevents drug escape;

a drug transporting means in the housing that contains a metering chamber of volume corresponding to a desired dose of the drug and that is movable from a load position, in which it communicates with the drug reservoir to receive in its metering chamber drug from the drug reservoir, to a release position in which it communicates with the air outlet passage to release drug from the metering chamber into the air outlet passage; and a vacuum generating means that creates a partial vacuum in the metering chamber of the drug transporting means when it is in its load position to draw drug into the metering chamber from the drug reservoir.

The inhaler provides the advantage that the drug is assisted into the metering chamber by means of a pressure difference between the drug reservoir and the metering chamber. Therefore additional force is applied on the drug particles to cause them to flow into the metering chamber. This will increase the accuracy and reproducibility by reducing blockage. Also, since gravity alone is not responsible for feeding the drug into the transporting means, reasonable accuracy of metering is obtainable even if the inhaler is not correctly held.

Preferably the vacuum generating means comprises a piston which travels in a vacuum chamber in the housing and defines one wall of the vacuum chamber; the piston reducing the air pressure behind it as it increases the volume of the vacuum chamber.

The drug transporting means may be a slide that slides between its load position and its release position in a slide passage in the housing; the slide fitting snugly in the slide passage. In this way drug particles are prevented from escaping between the slide and the walls of the slide passage.

Preferably the metering chamber is an aperture through the slide; one mouth of the aperture connecting to the drug reservoir and the opposite mouth of the aperture connecting to the vacuum generating means when the slide is in the load position.

Preferably the slide is connected to the piston so that the slide and piston move synchronously to provide the greatest vacuum when the slide reaches the load position.

Preferably a vacuum passage connects the slide passage to the vacuum chamber; the mouth of the vacuum passage in the slide passage being sealed by an air permeable filter to prevent the escape of drug from the metering chamber; and the opposite mouth of the vacuum passage opening into the vacuum chamber immediately before the position of furthest extension of the piston.

The inhaler may further comprise an actuator; the triggering of which causes the drug transporting means to move to its load position and the vacuum generating means to generate a vacuum.

Preferably the inhaler further comprises a biasing means to bias the drug transporting means to its release position.

Baffles may be included in the air outlet passage to promote entrainment of drug particles deposited in it.

The air permeable filters used in the inhaler preferably have a pore size small enough to resist the ingress of bacteria. Therefore the pore size is preferably in the range of 1 $\mu$m to 50 $\mu$m, more preferably in the range of 5 $\mu$m to 25 $\mu$m and even more preferably in the range of 10 $\mu$m to 20 $\mu$m. Filters having pores of this size will also prevent the escape of drug particles since these are unlikely to pass through a pore of size of less than 100 $\mu$m.

In use sufficient drug may be filled into the reservoir to provide a user of the inhaler with a large number (for example 200) of metered doses of the drug. Once the user has used up all of the drug, the inhaler is disposed of or is recycled. The user then obtains another filled, inhaler. This has the advantage that the user is not required to continuously load capsules or like into the inhaler.

The inhaler may be used as a pulmonary inhaler or a nasal inhaler; although the preferred use is as a pulmonary inhaler.

In another aspect this invention provides an inhaler as defined above that contains a powdered medicament in the reservoir.

Preferably the powdered medicament is suitable for the treatment of asthma by pulmonary inhalation. Medicaments of this type are well known. More preferably the medicament is the orthorhombic crystal form of Ciclosporin disclosed in EP 0 504 760 A.

Embodiments of the invention are now described, by way of example only, with reference to the drawings in which:

FIG. 1 is a side view of an inhaler;

FIG. 2 is an end view of the inhaler of FIG. 1;

FIG. 3 is a cross-section taken along line A—A' in FIG. 2 illustrating the inhaler in its release position;

FIG. 4 is a similar cross-section illustrating the inhaler in its load position;

FIG. 5 is a cross-section taken along line B—B' of FIG. 3;

FIG. 6 is a cross-section taken along line A—A' of FIG. 2 but without the moving parts shown;

FIG. 7 is a cross-section illustrating a one way valve in its closed position; and FIG. 8 is a cross-section illustrating the one way valve in its open position.

The inhaler comprises a cylindrical housing 2 having a drug reservoir 4 extending normally from its side. A mouth piece 6 projects from a front end 10 of the housing 2; flush with the side of the housing 2 and in alignment with the drug reservoir 4. A cylindrical button 8 also projects from the front end 10 of the housing 2 at a position slightly off-centre; away from the mouth piece 6.

Figure 4:
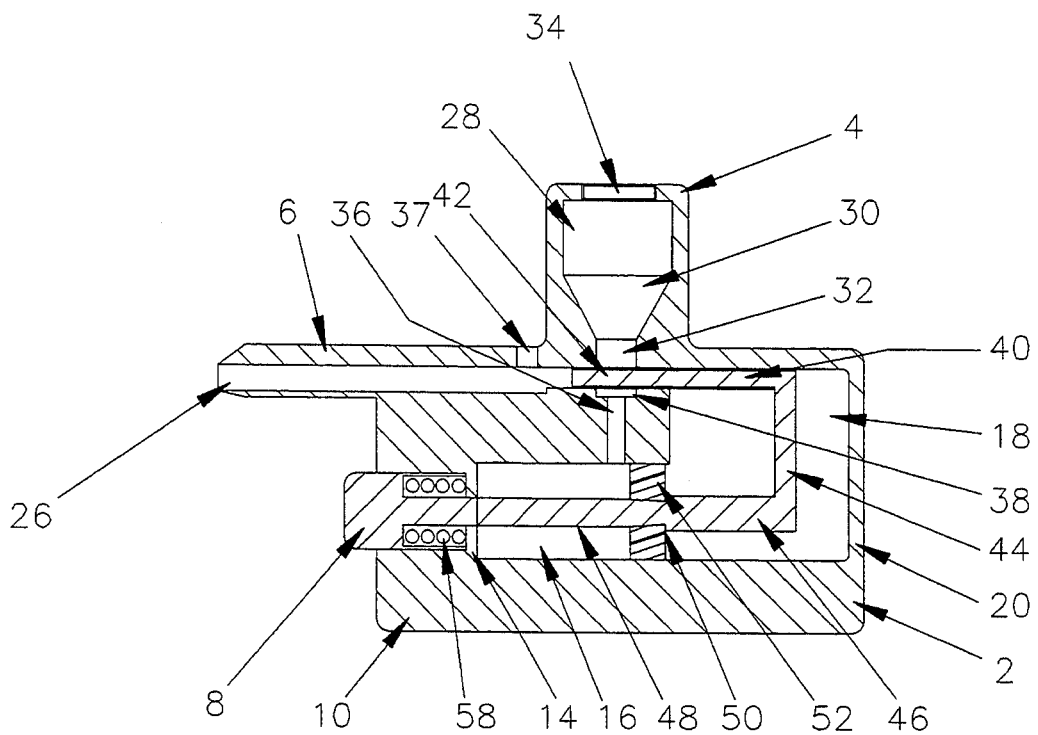
Figure 5:
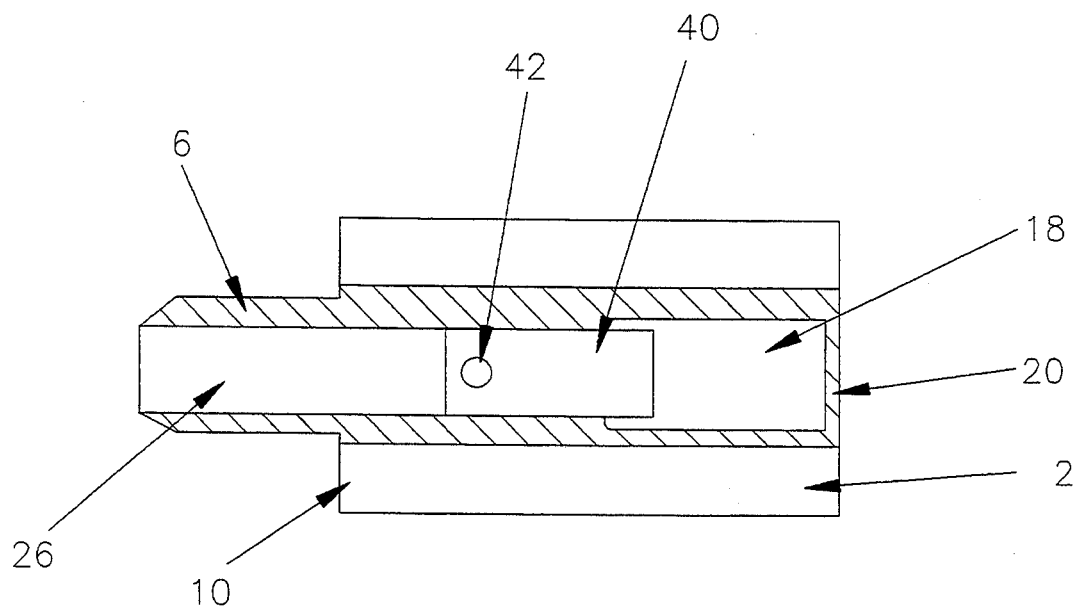
Figure 6:
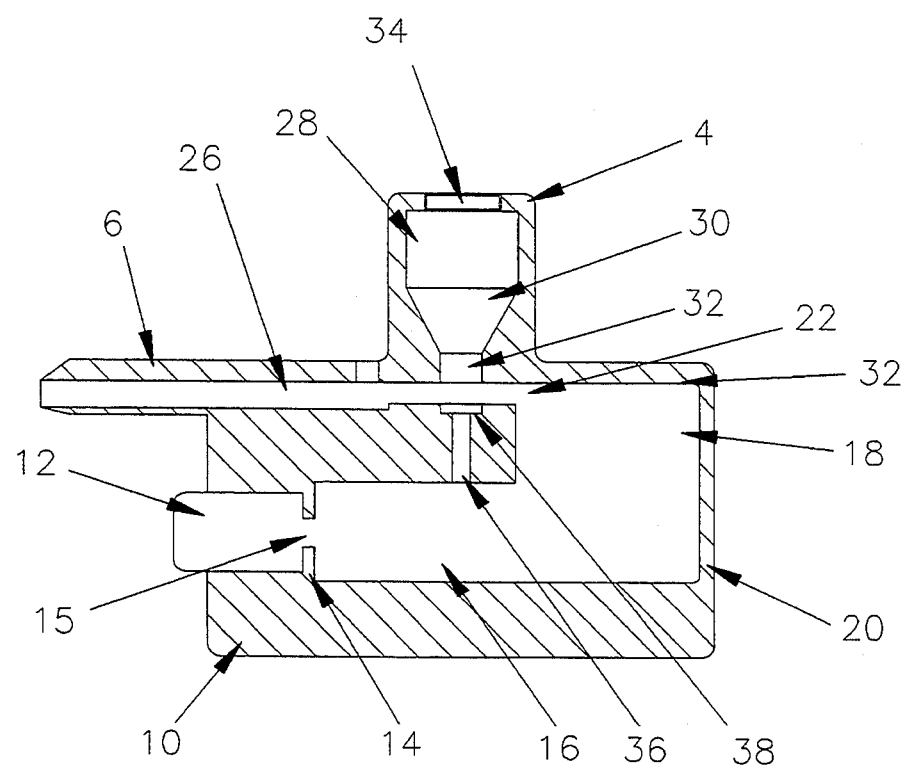

The housing 2 has a cylindrical bore 12 in its front end 10, beneath the button 8 and into which the button 8 may move. The bore 12 has a depth sufficient to receive at least most of the button 8 in it. This is best illustrated in FIG. 4. The diameter of the bore 12 is slightly larger than the diameter of the button 8 so that the button 8 may move freely but snugly in it. The bore 12 terminates in an inwardly extending, annular shoulder 14.

A cylindrical vacuum chamber 16 extends rearwardly from the shoulder 14 to a position rear of the drug reservoir 4. The longitudinal axis of the vacuum chamber 16 aligns with the longitudinal axis of the bore 12. The diameter of the vacuum chamber 16 is shown to be slightly larger than the diameter of the bore 12 but need not be. The diameter of the aperture 15 connecting the bore 12 and the vacuum chamber 16 is much less than the diameter of the bore 12.

The rear end of the vacuum chamber 16 opens up into a working chamber 18. The working chamber 18 is substantially rectangular-parallelepiped in shape and extends rearwardly to the closed rear end 20 of the housing 2 and upwardly to just beneath the drug reservoir 4. A slide passage 22 of rectangular cross-section extends forwardly from the front edge of the working chamber 18, substantially flush with the upper edge 24 of the working chamber 18. The slide passage 22 terminates in an air outlet passage 26 which extends to the end of the mouth piece 6. The air outlet passage 26 is of slightly larger cross-section than the slide passage 22 so that a step-down, from the end of the slide passage 22 to the floor of the air outlet passage, is defined. An air inlet 37 opens into the air outlet passage 26 adjacent its join with the slide passage 22.

The drug reservoir 4 has a storage chamber 28 in it; the lower portion of the storage chamber 28 being in the form of a hopper 30. The hopper 30 terminates in a delivery passage 32 which itself terminates in the slide passage 22. The distal end of the drug reservoir 4 is sealed with an air permeable and bacterial resistant filter 34. Plainly the pores of the filter are sufficiently small to prevent drug escape. A suitable example of such a filter is that sold under the trade name POREX 4920 by Porex Technologies of Fairburn, USA. This filter has a pore size of about 20 μm.

A vacuum passage 36 connects the slide passage 22 and the vacuum chamber 16. The longitudinal axis of the vacuum passage 36 is aligned with that of the delivery passage 32. The mouth of the vacuum passage 36 in the slide passage 22 is sealed with an air permeable filter 38. A suitable filter is that sold under the trade name POREX X4949UF by Porex Technologies of Fairburn, USA. This filter has a pore size of about 10 μm.

An elongate slide 40 is positioned in the slide passage 22 and is of dimension so that it is snugly received in the slide passage 22 but is still able to slide freely in the slide passage 22. A metering aperture 42 extends through the slide 40 adjacent its front end. The metering aperture 42 is of a diameter equal to or slightly larger than the diameter of the delivery passage 32. The size of the metering aperture 42 is selected so that its volume corresponds to a specific dosage of the drug. Preferably the volume is such that 5 to 20 mg of the drug are contained in the metering aperture 42; and more preferably 10 to 15 mg.

The rear end of the slide 40 connects to the shorter arm 44 of an L-shaped support 46. The longer arm 48 of the support 46 extends along the longitudinal axis of the vacuum chamber 16, through the aperture 15 and connects to the button 8. The longer arm 48 is cylindrical and is of diameter so that it seals, in an air-tight manner, the aperture 15 but is still able to slide freely through the aperture 15. If necessary, ring seals or the like (not shown) may be formed into the shoulder 14.

A circumferential groove 50 is formed into the longer arm 48, intermediate its length, to provide a seat for a cylindrical rubber seal 52. The rubber seal 52 is of diameter to sealingly engage the inner walls of the vacuum chamber 16 in the manner of a syringe seal.

Figure 7:
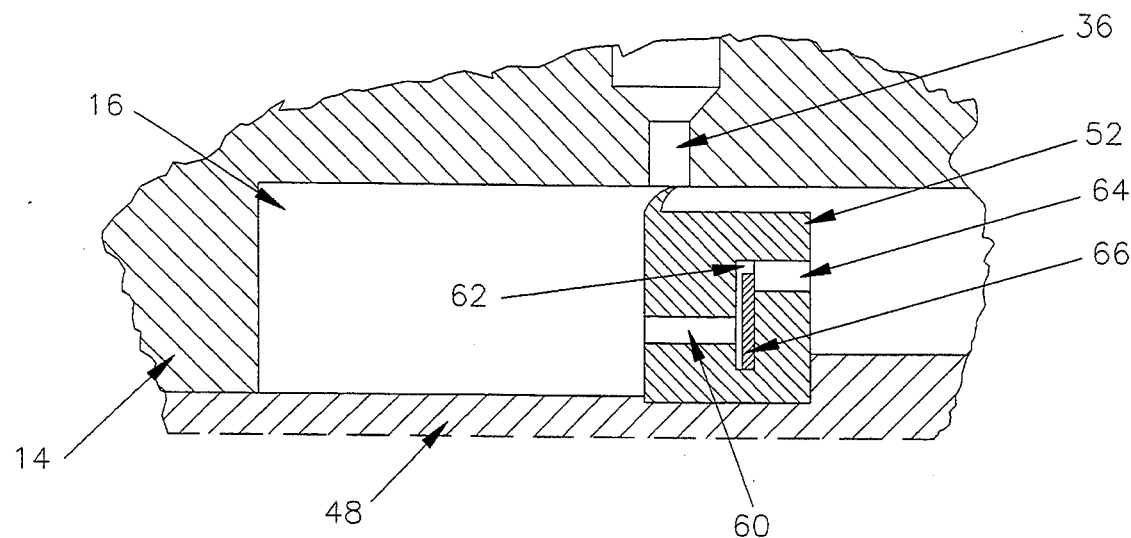
Figure 8:
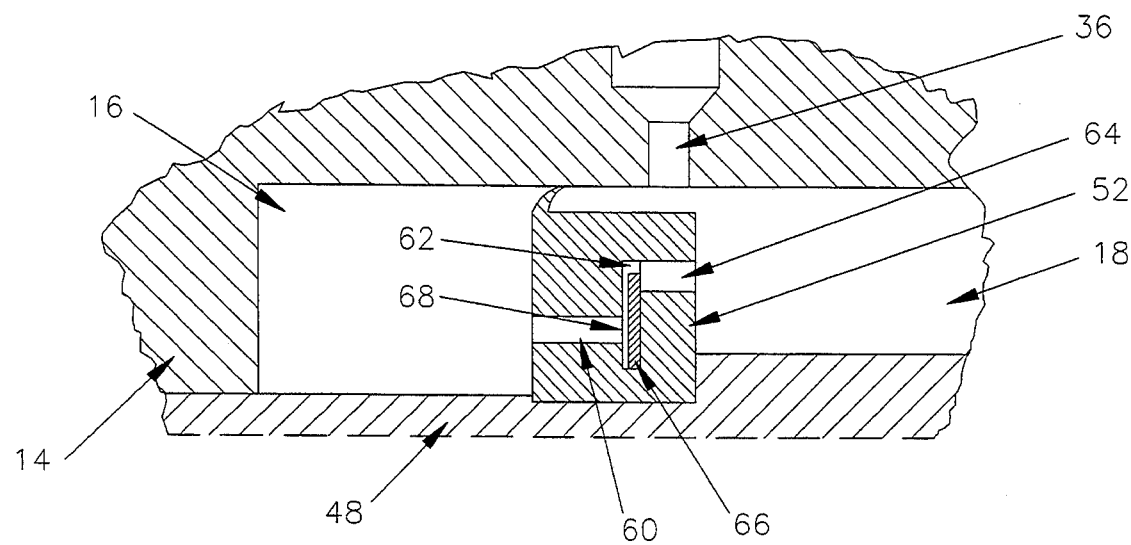

As is best illustrated in FIGS. 7 and 8, an inlet valve passage 60 extends into the rubber seal 52 from the vacuum chamber 16. The inlet valve passage 60 terminates in a radially extending valve seal chamber 62. The valve seat chamber 62 is connected by an exhaust valve passage 64 to the working chamber 18. The inlet valve passage 60 and the exhaust valve passage 64 run parallel to each other but are not aligned. A valve flap 66 is positioned in the valve seat chamber 62 and is able to move towards and away from the mouth 68 of the inlet valve passage 60.

If the vacuum chamber 16 is evacuated, the valve flap 66 is drawn over and seals the mouth 68 of the inlet valve passage 60. This is illustrated in FIG. 7. However if the pressure in the vacuum chamber 16 is higher than that of the working chamber 18, the valve flap 66 is forced away from the mouth 68 to release air from the vacuum chamber 16. In this way, a one-way valve that prevents pressure build up in the vacuum chamber is provided. Although only one one-way valve is shown, the embodiment illustrated has four of the one-way valves in the rubber seal 52. Of course, any number of valves can be used.

The button 8 has a flange 54 depending from its rear end to provide an annular recess 56 between the flange 54 and the longer arm 48. A spring 58 is fitted about the longer arm 48, between the button 8 and the shoulder 14. A portion of the spring 58 extends into the annular recess 56. When the button 8 is fully pushed into the bore 12, the entire spring 58 is received in the annular recess 56 (as is best illustrated in FIG. 4).

Figure 3:
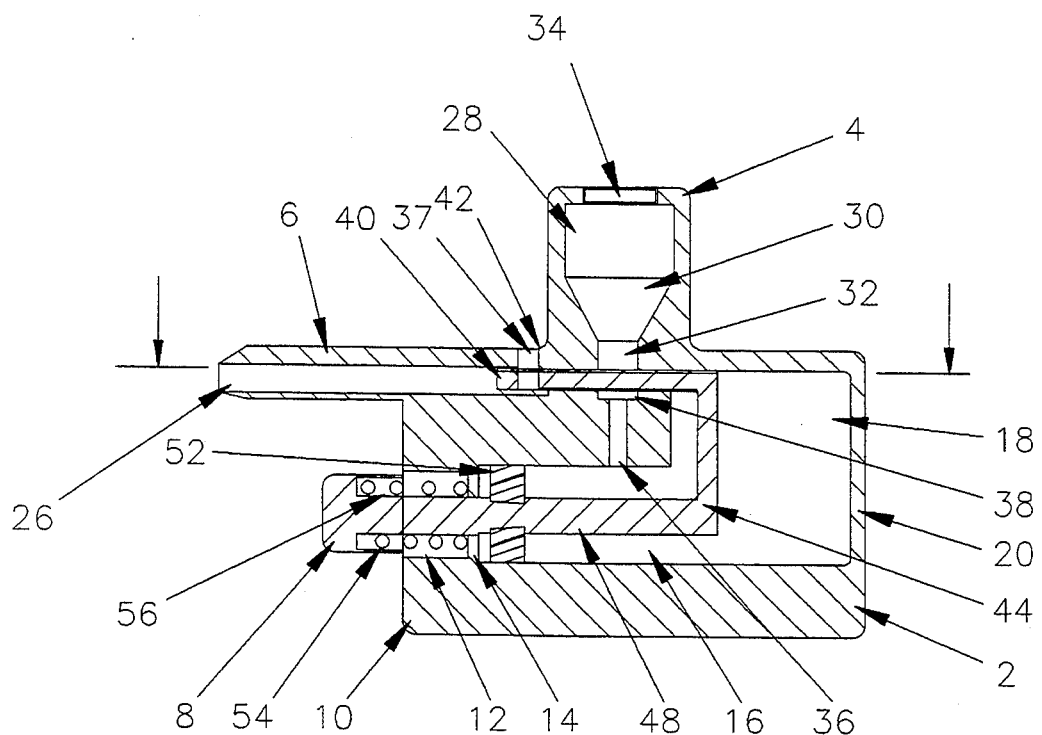

The support 46, the slide 40 and the rubber seal 52 are dimensioned and positioned so that, when the button 8 is fully extended from the bore 12 (as is best illustrated in FIG. 3), the rubber seal 52 is adjacent the shoulder 14 and the metering aperture 42 of the slide 40 is in the air outlet passage 26, beneath the air inlet 37. This is referred to as the release position of the slide. When the button 8 is fully pressed into the bore 12, the rubber seal 52 is positioned rearwardly of the vacuum passage 36 and the metering aperture 42 of the slide 40 is aligned between the delivery passage 32 of the drug reservoir 4 and the mouth of the vacuum passage 36. This is referred to as the load position of the slide 40.

In use, a particulate drug is stored in the storage chamber 28 of the drug reservoir 4. If the inhaler is held so that it is orientated as shown in the drawings, the drug will tend to flow, under the action of gravity, into the delivery passage 32. This flow will be facilitated by the hopper 30. The slide 40 however prevents the drug from flowing out of the delivery passage 32. The drug therefore is held in the drug reservoir 4 between the slide 40, at one end, and the filter 34 at the opposite end.

To use the inhaler, the user presses in the button 8. As the button 8 is pressed in, the support 46 is moved rearwardly; dragging the rubber seal 52 and the slide 40 with it. Since the seal between the longer arm 48 and the annular shoulder 14 is air-tight and the rubber seal 52 engages the wall of the vacuum chamber 16 in an air-tight manner, a partial vacuum forms in the vacuum chamber 16.

Once the rubber seal 52 moves past the vacuum passage 36, air flows into the inhaler through the filter 34, through the delivery passage 32 of the drug reservoir 4, through the metering aperture 42 of the slide 40 and into the vacuum passage 36 and the vacuum chamber 16 to equalize the pressure in the vacuum chamber 16. This flow of air assists transport of the particulate drug down the delivery passage 32 and into the metering aperture 42 of the slide 40. The particulate drug is prevented from falling further by the filter 38 in the mouth of the vacuum passage 36.

Once the pressure on the button 8 is released, the spring 58 forces the button 8 outwardly. This drags the support 46 and hence the slide 40 towards the front end 10 of the inhaler. The movement of the slide 40 causes the portion of the drug that is contained in the metering aperture 42 to move with it. This portion of the drug is prevented from escaping from the metering aperture 42 by the snug fit of the slide 40 in the slide passage 22. Also once the metering aperture 42 is moved from under the delivery passage 32 of the drug reservoir 4, the slide 40 prevents further drug from leaving the drug reservoir 4.

When the slide 40 reaches its release position, the drug is able to fall from the metering aperture 42 into the air outlet passage 26. The user then inhales causing air to flow into the outlet passage 26 through the air inlet 37. The drug in the air outlet passage 26 is then entrained and flows with the air into the user's mouth and lungs. To provide for better entrainment of the drug, baffles may be provided in the outlet passage 26.

As the rubber seal 52 moves towards the shoulder 14 it causes a build up of pressure in the vacuum chamber 16. This pressure is released through the one-way valve in the rubber seal 52. Of course this one way valve need not be incorporated in the rubber seal 52, instead it can be incorporated in the walls of the vacuum chamber 16 or the shoulder 14.

The inhaler may be made from suitable plastic which is inert, odourless and free from extractables. Thermoplastics are preferred because they can be injection moulded. Suitable thermoplastics are high density polyethylene, polystyrene and the polyacetal sold under the trade name DELRIN by E. I. du Pont de Nemours of Wilmington, Delaware, USA. However the material selected will depend upon the drug used. The volume of the drug reservoir 4 should be selected so that the user is provided with an amount of the drug that gives an adequate duration of use. Amounts corresponding to 100 to 200 doses are contemplated. Of course the amount chosen will depend upon the drug and its stability. The drug reservoir 4 is preferably made of clear plastic or has a clear plastic segment so that the user can determine how much drug remains in the drug reservoir 4.

The inhaler provides the significant advantage that a particulate drug may be stored in bulk in it without the reproducibility of dosing being significantly adversely affected. Blockages and agglomerations of the drug particles that would normally occur are significantly reduced by the vacuum assisted transport of the drug. Plainly certain drugs will be too "sticky" for use in the inhaler but these drugs would not ordinarily be used in inhalers.

The invention is plainly not limited to the embodiment described above since many modifications can be made without departing from the scope of the invention. For example the slide 40 may have more then one metering aperture 42 and the housing 4 may have more then one drug reservoir 4. Similarly, more than one slide 40 may be provided. The means of developing the pressure difference between the metering aperture 42 and the drug reservoir 4 need not be the syringe-like mechanism shown. Instead any suitable means of generating a vacuum may be used. Also the slide 40 need not be linear, it can also be arcuate. In this case, the slide passage 22 will be arcuate. Alternatively the slide 40 may be in the form of a quadrant or similar segment that rotates between the load and release positions.

What is claimed is:

1. An inhaler for delivering metered doses of a particulate drug, the inhaler comprising a housing having an air inlet and an air outlet passage communicating with the air inlet for entraining the particulate drug in a stream of air traveling through said housing;

a drug reservoir attached to the housing to contain multiple doses of the particulate drug, the drug reservoir having an air permeable portion that permits air flow into the drug reservoir but prevent drug escape;

a drug transporting means in the housing that has a metering chamber of volume corresponding to a desired dose of the drug, the drug transporting means being operative between a load position, in which it communicates with the drug reservoir to receive in its metering chamber drug from the drug reservoir, and a release position in which it releases drug transported from the metering chamber into the air outlet passage;

a vacuum generating means that creates a partial vacuum in the metering chamber of the drug transporting means when it is in its load position to draw drug into the metering chamber from the drug reservoir; and an acutator means connected to the drug transporting means and the vacuum generating means for causing movement of the drug transporting means to its load position and for simultaneously causing the vacuum generating means to create a partial vacuum.

2. An inhaler according to claim 1 in which the vacuum generating means comprises a piston which travels in a vacuum chamber in the housing and defines one wall of the vacuum chamber; the piston reducing the air pressure behind it as it increases the volume of the vacuum chamber.

3. An inhaler according to claim 1 in which the drug transporting means is a slide that slides reciprocatingly between its load position and its release position in a slide passage in the housing; the slide fitting snugly in the slide passage to prevent escape of drug.

4. An inhaler according to claim 3 in which the metering chamber is an aperture through the slide; one mouth of the aperture connecting to the drug reservoir and the opposite mouth of the aperture connecting to the vacuum generating means when the slide is in the load position.

5. An inhaler according to claim 2 in which the drug transporting means is a slide that slides reciprocatingly between its load position and its release position in a slide passage in the housing; the slide fitting snugly in the slide passage to prevent escape of drug.

6. An inhaler according to claim 5 in which the metering chamber is an aperture through the slide; one mouth of the aperture connecting to the drug reservoir and the opposite mouth of the aperture connecting to the vacuum generating means when the slide is in the load position.

7. An inhaler according to claim 5 in which the slide is connected to the piston so that the slide and piston move synchronously to provide the greatest vacuum when the slide reaches the load position.

8. An inhaler according to claim 7 in which a vacuum passage connects the slide passage to the vacuum chamber; the mouth of the vacuum passage in the slide passage being sealed by an air permeable filter to prevent the escape of drug from the metering chamber; and the opposite mouth of the vacuum passage opening into the vacuum chamber immediately before the position of furthest extension of the piston.

9. An inhaler according to claim 1 further comprising a biasing means to bias the drug transporting means to its release position.

10. An inhaler according to claim 1 further comprising baffles in the air outlet passage to promote entrainment of drug particles deposited in it.

11. An inhaler according to claim 1 in which the reservoir contains a powdered drug.

12. An inhaler according to claim 11 in which the powdered drug is suitable for the treatment of asthma by pulmonary inhalation.

* * * * *